United States Patent [19]

Saito et al.

[11] Patent Number: 4,698,336
[45] Date of Patent: Oct. 6, 1987

[54] 3-(PYRROLIDINIO)METHYL-3-CEPHEM DERIVATIVES

[75] Inventors: Isao Saito; Seiichiro Nomoto; Takashi Kamiya; Hiroshi Yamauchi; Isao Sugiyama; Yoshimasa Machida; Shigeto Negi, all of Ibaraki, Japan

[73] Assignee: Eisai Co., Ltd., Tokyo, Japan

[21] Appl. No.: 821,914

[22] Filed: Jan. 23, 1986

[30] Foreign Application Priority Data

Jan. 30, 1985 [JP] Japan .................................. 60-14529
Jan. 30, 1985 [JP] Japan .................................. 60-14530

[51] Int. Cl.$^4$ ................... A61K 31/545; C07D 501/46
[52] U.S. Cl. ...................................... 514/202; 540/222
[58] Field of Search ........................... 544/22; 514/202

[56] References Cited

U.S. PATENT DOCUMENTS 4,406,899 9/1983 Aburaki et al. ..................... 514/202
4,525,473 6/1985 Aburaki et al. ..................... 514/202

FOREIGN PATENT DOCUMENTS 0062321 10/1982 European Pat. Off. ............ 514/202

Primary Examiner—Donald G. Daus
Assistant Examiner—Barbara Cassatt
Attorney, Agent, or Firm—Wenderoth, Lind & Ponack

[57] ABSTRACT

Described herein is 3-(pyrrolidinio)methyl-3-cephem derivative represented by the general formula:

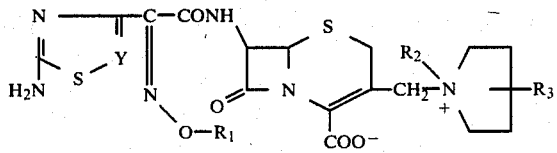

wherein Y stands for CH or nitrogen atom, $R_1$ and $R_2$ are the same or different, and represent a lower alkyl group, $R_3$ denotes a hydroxy-substituted lower alkyl group, a lower alkyl group, or a carbamoyl group, and when Y stands for CH, $R_3$ denotes a hydroxy-substituted lower alkyl group. The derivative is useful as antibacterial composition. Also described herein are process for the production of the derivative and antibacterial composition.

7 Claims, No Drawings

3-(PYRROLIDINIO)METHYL-3-CEPHEM DERIVATIVES

BACKGROUND OF THE INVENTION

1. Field of the Invention

This invention relates to novel 3-(pyrrolidinio)methyl-3-cephem derivatives useful as antibacterial composition, process for the production thereof, and antibacterial composition.

2. Description of the Prior Art

As compounds containing a (pyrrolidinio)methyl group at the 3-position of the cephem skeleton, there have heretofore been known the compounds described in U.S. Pat. No. 4,406,899 and U.S. Pat. No. 4,525,473.

SUMMARY OF THE INVENTION

The present inventors have found that the compounds of this invention possess excellent antibacterial activities, leading the completion of this invention.

Therefore, an object of the present invention is to provide novel compounds useful as antibacterial compositions and a process for the production thereof as well as their use as antibacterial composition.

DESCRIPTION OF THE INVENTION

The compounds of this invention are defined as follows: 3-(pyrrolidinio)methyl-3-cephem derivatives represented by the general formula:

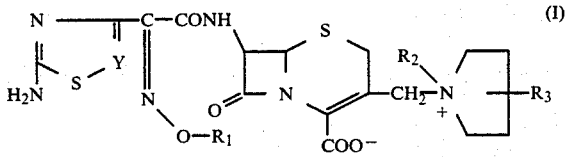

wherein Y stands for CH or nitrogen atom, $R_1$ and $R_2$ are the same or different, and represent a lower alkyl group, $R_3$ denotes a hydroxy-substituted lower alkyl group, a lower alkyl group, or carbamoyl group, and when Y stands for CH, $R_3$ denotes a hydroxy-substituted lower alkyl group, or pharmaceutically acceptable salt thereof. The term "lower" is used to define a group having 1 to 6 carbon atom(s), unless otherwise provided.

In the above-described general formula (I), examples of the lower alkyl group for $R_1$, $R_2$ and $R_3$ include methyl, ethyl, n-propyl, i-propyl, n-butyl, t-butyl, sec-butyl, and the like. Further, examples of the hydroxy-substituted lower alkyl group for $R_3$ include hydroxymethyl, 2-hydroxyethyl, 1-hydroxyethyl, 3-hydroxypropyl, 4-hydroxybutyl, and the like.

As the pharmaceutically acceptable salts of the compounds shown by the general formula (I), there are salts that are pharmaceutically acceptable; for example, inorganic acid salts such as hydrochloride, hydrobromide, hydroiodide, sulfate, carbonate, bicarbonate, and the like; organic carboxylic acid salts such as maleate, lactate, tartarate, and the like; organic sulfonic acid salts such as methanesulfonate, benzensulfonate, toluenesulfonate, and the like; amino acid salts such as aspartate, glutamate, and the like.

With respect to configuration of the following group:

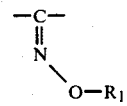

in the compounds of this invention shown by the general formula (I), there exist syn-isomer (Z) and anti-isomer (E). This invention includes both isomers but the syn-isomer is preferable from an antibacterial viewpoint.

Also, with respect to configuration of the group:

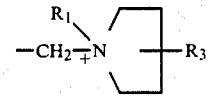

there exist isomers; the present invention includes all of the isomers.

The compounds of this invention can be produced by the following process:

A compound represented by the general formula:

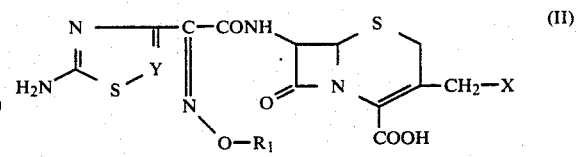

wherein Y and $R_1$ have the same meanings as defined above, and X represents a halogen atom, a compound wherein the amino group and/or carboxyl group is/are protected by a protective group, or a salt thereof, is reacted with a compound represented by the general formula:

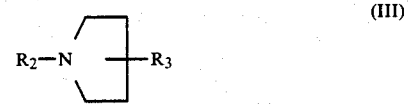

wherein $R_2$ and $R_3$ have the same meaning as defined above, or with salt thereof, followed by optionally removing the protective group to produce the compounds represented by the general formula (I) and a pharmaceutically acceptable salt thereof.

As the halogen atom for X in the above-described general formula (II), there may be mentioned iodine, bromine and chlorine atom, but in particular, iodine and bromine are preferable.

The above-described reaction can be carried out at reaction temperature of $-40°$ to $60°$ C., preferably $-30°$ to $40°$ C. As solvents for the reaction, anhydrous organic solvents are desired. Examples of the organic solvents which may be used include lower alkylnitriles such as acetonitrile, propionitrile, and the like; halogenated lower alkyls such as chloromethane, dichloromethane, chloroform, and the like; ethers such as tetrahydrofuran, dioxane, and the like; amides such as N,N-dimethyl-formamide, and the like; esters such as ethyl acetate, and the like; ketones such as acetone, and the like; hydrocarbons such as benzene, and the like; or solvent mixtures thereof.

As the salts of the compounds represented by the general formulae (II) and (III), and as the protective groups of the amino group and carboxyl group for the compounds represented by the general formula (II), there may be used any conventional salts and groups, as long as they do not disturb the reaction described above.

Examples of the protective groups of the amino groups include formyl group, acetyl group, chloroacetyl group, dichloroacetyl group, t-butoxycarbonyl group, benzyloxycarbonyl group, trityl group, p-methoxybenzyl group, diphenylmethyl group, and the like. Examples of the protective groups for the carboxy group include p-methoxybenzyl group, p-nitrobenzyl group, t-butyl group, methyl group, 2,2,2-trichloroethyl group, diphenylmethyl group, pivaloyloxymethyl group, and the like. It is advantageous to use silylating agents such as bis(trimethylsilyl)-acetamide, N-methyl-N-(trimethylsilyl)acetamide, N-methyl-N-(trimethylsilyl)trifluoroacetamide, and the like, because both the amino group and the carboxy group can be protected simultaneously.

The removal of protective groups may be achieved in accordance with a conventional procedure such as hydrolysis, reduction and the like, depending on type of the protective group used.

As the salts of the compounds represented by the general formulae (II) and (III), there may be mentioned alkali metal salts such as sodium salts, potassium salts, and the like; alkaline earth metal salts such as calcium salts, magensium salts, and the like; ammonium salts; inorganic acid salts such as hydrochlorides, hydrobromides, sulfates, carbonates, hydroiodides, bicarbonates, and the like; organic carboxylic acid salts such as acetates, trifluoro-acetates, maleates, lactates, tartarates, and the like; organic sulfonic acid salts such as methanesulfonates, benzenesulfonates, toluenesulfonates, and the like; amine salts such as trimethyl amine salts, triethyl amine salts, pyridine salts, procain salts, picoline salts, dicyclohexyl amine salts, N,N'-dibenzylethylenediamine salts, N-methylglucamine salts, diethanolamine salts, triethanolamine salts, tris(hydroxymethylamine)methane salts, phenethylbenzylamine salts, and the like; amino acid salts such as arginates, aspartates, lysine salts, glutaminates, serine salts, and the like; from which the salt may be appropriately chosen.

The compounds of this invention exhibit a strong antibacterial activity against both gram-positive and gram-negative bacteria. Acute toxicity [$LD_{50}$ (mouse, intravenous injection)] of the following compounds was more than 3 g/kg.

7β-[2-(5-Amino-1,2,4-thiadiazol-3-yl)-(Z)-2-methoxyimino-acetamido]-3-[(2S)-hydroxymethyl-(1S)-methylpyrrolidinio]-methyl-3-cephem-4-carboxylate, 7β-[2-(5-Amino-1,2,4-thiadiazol-3-yl)-(Z)-2-methoxyiminoacetamido]-3-[(2S)-carbamoyl-(1S)-methylpyrrolidinio]methyl-3-cephem-4-carboxylate, 7β-[2-(5-Amino-1,2,4-thiadiazol-3-yl)-(Z)-2-methoxyiminoacetamido]-3-[(1S,2R)-dimethylpyrrolidinio]-methyl-3-cephem-4-carboxylate, 7β-[2-(2-Aminothiazol-4-yl)-(Z)-2-methoxyiminoacetamido]-3-[(2S)-hydroxymethyl-(1S)-methylpyrrolidinio]methyl-3-cephem-4-carboxylate.

An antibacterial composition containing the compound of this invention is used for mammals including humans. Their dosages are 2 to 300 mg/kg/day, or preferably 10 to 100 mg/kg/day.

The antibacterial composition may be administered orally in the form of powders, granules, capsules, tablets, and the like, or parenterally in the form of injections, suppositories, and the like. These compositions may be prepared in a conventional manner using an effective amount of the compound of this invention and a pharmaceutically acceptable carrier or excipient.

This invention will be described in more detail by means of the following examples.

EXAMPLE 1

7β-[2-(5-Amino-1,2,4-thiadiazol-3-yl)-(Z)-2-methoxyiminoacetamido]-3-[(2S)-hydroxymethyl-(1S)-methylpyrrolidinio]methyl-3-cephem-4-carboxylate (Compound 1-A):

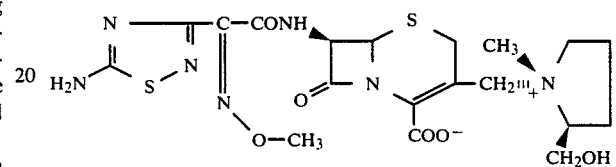

7β-[2-(5-Amino-1,2,4-thiadiazol-3-yl)-(Z)-2-methoxyiminoacetamido]-3-[(2S)-hydroxymethyl-(1R)-methylpyrrolidinio]methyl-3-cephem-4-carboxylate (Compound 1-B):

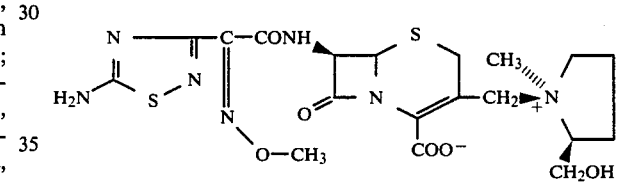

A mixture of 7β-[2-(5-amino-1,2,4-thiadiazol-3-yl)-(Z)-2-methoxyiminoacetamido]-3-acetoxymethyl-3-cephem-4-carboxylic acid (5.21 g), N-methyl-N-(trimethylsilyl)trifluoroacetamide (21.2 ml) and dichloromethane (250 ml) was stirred and dissolved. Under ice cooling, iodotrimethylsilane (4.55 ml) was added to the solution. The mixture was stirred at the same temperature for 5 minutes and at room temperature for 15 minutes. The solution was concentrated under reduced pressure to obtain silylated 7β-[2-(5-amino-1,2,4-thiadiazol-3-yl)-(Z)-2-methoxyiminoacetamido]-3-iodomethyl-3-cephem-4-carboxylic acid.

The silylated product was dissolved in acetonitrile (31 ml), and the solution was cooled to −30° C. A solution of (2S)-hydroxymethyl-1-methylpyrrolidine (4.05 g) and N-methyl-N-(trimethylsilyl)trifluoroacetamide (6.95 ml) in acetonitrile (105 ml) was dropwise added to the resulting solution over 30 minutes. The mixture was stirred at the same temperature for a further minute. A mixture of methanol (15 ml) and acetonitrile (15 ml) was added to the reaction mixture and the formed precipitates were recovered by filtration. The precipitates were purified by silica gel column chromatography (eluent: water-methanol) to obtain a crude product.

Then the crude product was purified by reverse phase silica gel (ODS) column chromatography (eluent: water-methanol) to obtain the desired compounds, that is, Compound 1-A (801 mg) and Compound 1-B (88 mg).

It was determined by nuclear overhauser effect (NOE) that the obtained compounds had the above-described steric structure.

EXAMPLE 2

7β-[2-(5-Amino-1,2,4-thiadiazol-3-yl)-(Z)-2-methoxyiminoacetamido]-3-[(2S)-carbamoyl-(1S)-methylpyrrolidinio]methyl-3-cephem-4-carboxylate:

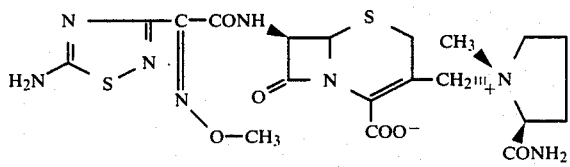

In dichloromethane (6 ml) was suspended 7β-[2-(5-amino-1,2,4-thiadiazol-3-yl)-(Z)-2-methoxyiminoacetamido]-3-acetoxymethyl-3-cephem-4-carboxylic acid (456 mg). To the suspension, N-methyl-N-(trimethylsilyl)trifluoroacetamide (0.63 ml) was added, followed by mixing and dissolving them. To the solution, was added under ice-cooling iodotrimethylsilane (0.384 ml). The mixture was stirred at the same temperature for 5 minutes and at room temperature for 15 minutes. The solution was concentrated under reduced pressure to obtain silylated 7β-[2-(5-amino-1,2,4-thiadiazol-3-yl)-(Z)-2-methoxyiminoacetamido]-3-iodomethyl-3-cephem-4-carboxylic acid.

The silylated product was dissolved in acetonitrile (3.6 ml). A solution of 1-methyl-(2S)-prolinamide (0.307 g) and N-methyl-N-(trimethylsilyl)trifluoroacetamide (0.445 ml), in acetonitrile (10 ml) was dropwise added to the resulting solution over 30 minutes under cooling to −30° C. The mixture was stirred at the same temperature for further 30 minutes. A mixture of methanol (1.8 ml) and acetonitrile (1.8 ml) was added to the reaction mixture and the formed precipitates were taken by filtration. The precipitates were purified twice by silica gel column chromatography (eluent: acetone-water) to obtain the desired product (79 mg).

EXAMPLE 3

7β-[2-(5-Amino-1,2,4-thiadiazol-3-yl)-(Z)-2-methoxyiminoacetamido]-3-[(1S,2R)-dimethylpyrrolidinio]-methyl-3-cephem-4-carboxylate:

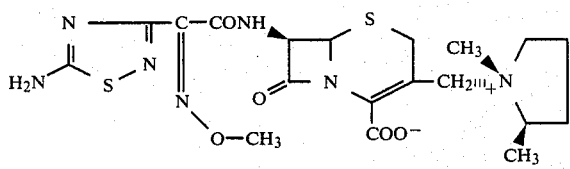

In dichloromethane (9 ml) was suspended 7β-[2-(5-amino-1,2,4-thiadiazol-3-yl)-(Z)-2-methoxyiminoacetamido]-3-acetoxymethyl-4-carboxylic acid (700 mg). To the suspension, N-methyl-N-(trimethylsilyl)trifluoroacetamide (1.14 ml) was added, followed by mixing and dissolving them. To the solution, iodotrimethylsilane (0.59 ml) was added under ice cooling. The mixture was stirred at the same temperature for 5 minutes and at room temperature for 15 minutes. The solution was concentrated under reduced pressure to obtain silylated 7β-[2-(5-amino-1,2,4-thiadiazol-3-yl)-(Z)-2-methoxyiminoacetamido]-3-iodomethyl-3-cephem-4-carboxylic acid.

The silylated product was dissolved in acetonitrile (4.5 ml). A solution of (R)-1,2-dimethylpyrrolidine (213 mg) in acetonitrile (5 ml) was dropwise added to the resulting solution over 1 hour under cooling to −30° C. The mixture was stirred at the same temperature for further 30 minutes. A mixture of methanol (0.7 ml) and acetonitrile (0.7 ml) was added to the reaction mixture and the formed precipitates were taken by filtration. The precipitates were purified by silica gel column chromatography (eluent: water-methanol) to obtain a crude product. Then the crude product was purified by reverse phase silica gel column (ODS) chromatography (eluent: water-methanol) to obtain the desired product (12 mg).

EXAMPLE 4

7β-[2-(5-Amino-1,2,4-thiadiazol-3-yl)-(Z)-2-methoxyiminoacetamido]-3-[2-(2-hydroxyethyl)-1-methylpyrrolidinio]methyl-3-cephem-4-carboxylate:

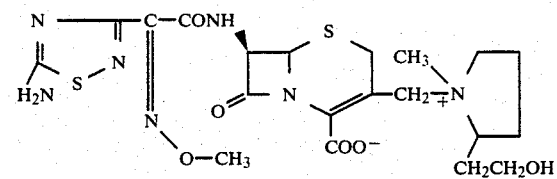

In dichloromethane (6 ml) was suspended 7β-[2-(5-amino-1,2,4-thiadiazol-3-yl)-(Z)-2-methoxyiminoacetamido]-3-acetoxymethyl-3-cephem-4-carboxylic acid (456 mg). To the suspension, N-methyl-N-(trimethylsilyl)trifluoroacetamide (0.63 ml) was added, followed by mixing and dissolving them. To the solution, iodotrimethylsilane (0.384 ml) was added under ice cooling. The mixture was stirred at the same temperature for 5 minutes and at room temperature for 15 minutes. The solution was concentrated under reduced pressure to obtain silylated 7β-[2-(5-amino-1,2,4-thiadiazol-3-yl)-(Z)-2-methoxyiminoacetamido]-3-iodomethyl-3-cephem-4-carboxylic acid.

The silylated product was dissolved in acetonitrile (3.6 ml). A solution of 1-methyl-2-pyrrolidinethanol (0.326 ml) and N-methyl-N-(trimethylsilyl)trifluoroacetamide (0.445 ml) in acetonitrile (10 ml) was dropwise added to the resulting solution over 32 minutes under cooling to −30° C. The mixture was stirred at the same temperature for further 26 minutes. A mixture of methanol (1.8 ml) and acetonitrile (1.8 ml) was added to the reaction mixture and the formed precipitates were taken by filtration. The precipitates were purified twice by silica gel column chromatography (eluent: acetone-water) to obtain the desired product (63 mg).

EXAMPLE 5

7β-[2-(2-Aminothiazol-4-yl)-(Z)-2-methoxyiminoacetoamido]-3-[(2S)-hydroxymethyl-(1S)-methylpyrrolidinio]methyl-3-cephem-4-carboxylate

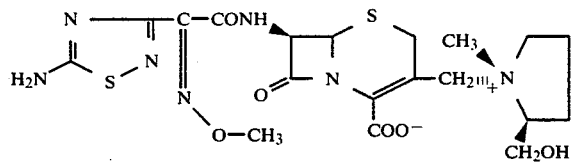

In dichloromethane (22 ml) was suspended 7β-[2-(2-aminothiazol-4-yl)-(Z)-2-methoxyiminoacetoamido]-3-acetoxymethyl-3-cephem-4-carboxylic acid (2.27 g). To the suspension, a solution of N-methyl-N-(trimethylsilyl)trifluoroacetamide (2.038 ml) in dichloromethane (2 ml) was added, followed by stirring and dissolving them. To the solution was added under ice-cooling a solution of iodotrimethylsilane (1.813 ml) in dichloromethane (2 ml), followed by stirring at the same temperature for 40 minutes. The resulting solution was concentrated under reduced pressure to obtain a silylated 7β-[2-(2-aminothiazol-4-yl)-(Z)-2-methoxyiminoacetoamido]-3-iodomethyl-3-cephem-4-carboxylic acid.

The silylated compound was dissolved in acetonitrile (13 ml), and tetrahydrofuran (0.4 ml) was added thereto. The solution was cooled to −30° C., and a solution of (2S)-hydroxymethyl-1-methyl-pyrrolidine (0.938 g) and N-methyl-N-(trimethylsilyl)trifluoroacetamide (1.51 g) in acetonitrile (10 ml) was dropped thereto over 45 minutes. The mixture was stirred at the same temperature for 60 minutes. To the reaction solution was added a mixture of methanol (2.27 ml) and acetonitrile (2.27 ml), and the formed precipitates were taken by filtration. The precipitates were purified twice by silica gel column chromatography (eluent: acetone-water), to obtain the desired product (35 mg).

TABLE 1

| Example No. | Infra Red Absorption Spectrum ($cm^{-1}$, Nujol) | Physical Property NMR (δ, DMSO-$d_6$) |
|---|---|---|
| 1-A | 1605, 1660, 1770 | 1.9~2.2(4H, m), 2.95(3H, S), 3.3~3.35(1H), 3.4~3.5(2H), 3.60(1H, m), 3.7~3.8(4H), 3.91(3H, s), 5.02(1H, d, J = 13 Hz), 5.11(1H, d, J = 5 Hz), 5.5(1H, b), 5.66(1H, dd, J = 5 Hz, 8 Hz), 8.13(2H, s), 9.52(1H, d, J = 8 Hz) |
| 1-B | 1605, 1655, 1765 | 1.9~2.2(4H, m), 2.92(3H, s), 3.65(1H, m), 3.7~3.8(3H), 3.91(3H, s), 4.24(1H, d J = 13 Hz), 4.78(1H, d, J = 13 Hz), 5.10(1H, d, J = 5 Hz), 5.5(1H, b), 5.66(1H, dd, J = 5 Hz, 8 Hz), 8.12(2H, s), 9.52(1H, dd, J = 8 Hz) |
| 2 | 1605, 1655, 1765 | 2.1~2.4(4H, m), 2.91(3H, s), 3.4(1H, m), 3.6~3.7(2H, m), 3.91(3H, s), 4.04(1H, d, J = 13 Hz), 4.88(1H, d, J = 13 Hz), 5.10(1H, d, J = 5 Hz), 5.66(1H, dd, J = 5 Hz, 8 Hz), 8.12(2H, s), 9.52(1H, d, J = 8 Hz) |
| 3 | 1605, 1655, 1765 | 1.30(3H, d, J = 6 Hz), 1.8~2.2(4H, m), 2.85(3H, s), 3.6~3.7(2H, m), 3.91(3H, s), 4.93(1H, d, J = 13 Hz), 5.12(1H, d, J = 5 Hz), 5.66(1H, dd, J = 5 Hz, 8 Hz), 8.1(2H, s), 9.50(1H, d, J = 8 Hz) |
| 4 | 1605, 1665, 1765 | 1.6~2.4(6H, m), 2.86(3H, s), 3.2~3.5(3H, m), 3.59(1H, d, J = 13 Hz), 3.62~3.67(3H, m), 3.83(1H, d, J = 16 Hz), 3.90(3H, s), 4.80(1H, b), 4.99(1H, d, J = 13 Hz), 5.12(1H, d, J = 5 Hz), 5.65(1H, d, J = 5 Hz, 8 Hz), 8.12(2H, s), 9.51(1H, d, J = 8 Hz) |
| 5 | 1600, 1655, 1765 | 1.9~2.2(4H, m), 2.95(3H, s), 3.65(1H, m), 3.83(3H, s), 5.05(1H, d, J = 13 Hz) 5.13(1H, d, J = 5 Hz), 5.64(1H, dd, J = 5 Hz, 8 Hz), 6.73(1H, s), 7.20(2H,s), 9.56(1H, d, J = 8 Hz) |

TABLE 2

Effect of the Invention
Antibacterial activities

| Sample Compound | Test Bacterium MIC (μg/ml) | | | | | | |
|---|---|---|---|---|---|---|---|
| | Staphylococcus aureus 209-P | Staphylococcus aureus E31106* | Escherichia coli NIHJ | Pseudomonas aeruginosa EP-01 | Serratia marcescens ES-75 | Pseudomonas maltophilia E04004 | Citrobacter freundii EC-34* |
| Example | | | | | | | |
| 1-A | 1.56 | 6.25 | 0.025 | 0.8 | 0.1 | 6.25 | 0.05 |
| 1-B | 1.56 | 12.5 | 0.1 | 1.56 | 0.1 | 6.25 | 0.1 |
| 2 | 1.56 | 12.5 | <0.025 | 1.56 | 0.1 | 3.13 | 0.05 |
| 3 | 1.56 | 12.5 | 0.2 | 1.56 | 0.2 | 6.25 | 0.2 |
| 5 | 0.8 | 25 | 0.05 | 3.13 | 0.1 | 12.5 | 0.05 |
| Control** Compound | 1.56 | 50 | 0.1 | 6.25 | 0.2 | 12.5 | 0.2 |

*β-Lactamase producing bacteria
**Control-Compound 7β-[2-(2-Aminothiadiaz ol-4-yl)-(Z)-methoxy-iminoaxcetamido-3-[(2S)—carbamoyl-(1S)—methylpyrrolidinio]methyl-3-cephem 4-carboxylate

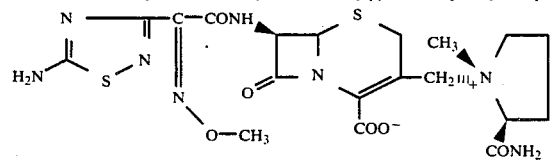

What is claimed is:

1. 3-(Pyrrolidinio)methyl-3-cephem compound of the formula:

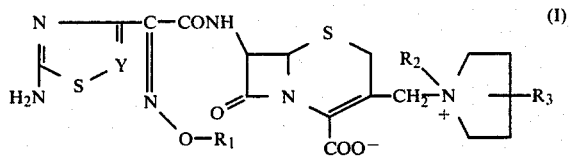

wherein Y stands for a nitrogen atom, $R_1$ and $R_2$ are the same or different, and represent a lower alkyl group, $R_3$ denotes a hydroxy-substituted lower alkyl group, a lower alkyl group, or carbamoyl group, or a pharmaceutically acceptable acid addition salt thereof.

2. The compound as claimed in claim 1, wherein

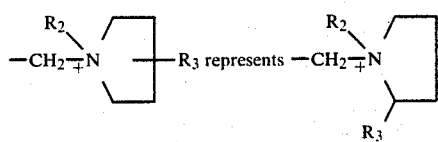

3. The compound as claimed in claim 2, wherein $R_3$ denotes a hydroxy-substituted lower alkyl group.

4. The compound as claimed in claim 2, wherein $R_1$ and $R_2$ stand each methyl group and $R_3$ denotes methyl group, hydroxymethyl group, hydroxyethyl group, or carbamoyl group.

5. The compound as claimed in claim 1, which is 7β-[2-(5-amino-1,2,4-thiadiazol-3-yl)-(Z)-2-methoxyiminoacetamido]-3-[(2S)-hydroxymethyl-(1S)-methylpyrrolidinio]methyl-3-cephem-4-carboxylate or a pharmaceutically acceptable acid addition salt thereof.

6. The compound as claimed in claim 1, which is 7β-[2-(5-amino-1,2,4-thiadiazol-3-yl)-(Z)-2-methoxyiminoacetamido]-3-[(2S)-carbamoyl-(1S)-methylpyrrolidinio]methyl-3-cephem-4-carboxylate or a pharmaceutically acceptable acid addition salt thereof.

7. An antibacterial composition comprising a pharmaceutically acceptable amount of a compound represented by the formula:

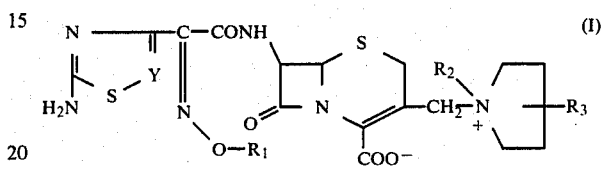

wherein Y represents a nitrogen atom, $R_1$ and $R_2$ are the same or different, and represent a lower alkyl group, $R_3$ denotes a hydroxy-substituted lower alkyl group, a lower alkyl group, or a carbamoyl group, or a pharmaceutically acceptable acid addition salt thereof, together with a pharmaceutically acceptable carrier or excipient.

* * * * *